US011207531B2

(12) United States Patent
Rondoni et al.

(10) Patent No.: US 11,207,531 B2
(45) Date of Patent: *Dec. 28, 2021

(54) HYBRID COMMUNICATION CHANNEL FOR COMMUNICATING WITH A MEDICAL DEVICE

(71) Applicant: Inspire Medical Systems, Inc., Golden Valley, MN (US)

(72) Inventors: John Rondoni, Plymouth, MN (US); Quan Ni, Shoreview, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 248 days.

This patent is subject to a terminal disclaimer.

(21) Appl. No.: 16/363,136

(22) Filed: Mar. 25, 2019

(65) Prior Publication Data

US 2019/0217105 A1 Jul. 18, 2019

Related U.S. Application Data

(63) Continuation of application No. 15/270,136, filed on Sep. 20, 2016, now Pat. No. 10,238,878, which is a
(Continued)

(51) Int. Cl.
*A61N 1/372* (2006.01)
*A61N 1/36* (2006.01)
(Continued)

(52) U.S. Cl.
CPC ........... *A61N 1/37252* (2013.01); *A61N 1/05* (2013.01); *A61N 1/3611* (2013.01);
(Continued)

(58) Field of Classification Search
CPC ...... A61N 1/05; A61N 1/0529; A61N 1/0551; A61N 1/3605; A61N 1/36078;
(Continued)

(56) References Cited

U.S. PATENT DOCUMENTS 7,270,633 B1 9/2007 Goscha
7,324,850 B2 1/2008 Persen et al.
(Continued)

FOREIGN PATENT DOCUMENTS

WO 0197907 12/2001
WO 2006034183 3/2006
(Continued)

OTHER PUBLICATIONS

Kiourti, "Biomedical Telemetry: Communication Between Implanted Devices and the External World", Opticon 1826 Issue 8, Spring 2010, pp. 1-7.
(Continued)

*Primary Examiner* — Christopher A Flory
(74) *Attorney, Agent, or Firm* — Dicke, Billig & Czaja, PLLC

(57) ABSTRACT

An apparatus comprises a communication channel comprising a plurality of disparate sequential communication links configured to facilitate bi-direction communication between an implantable medical device (IMD) and a programmer. A transceiver is configured to communicate with the programmer via a first communication link of the plurality of disparate communication links. A telemetry device is configured to communicate with the IMD via a second communication link of the plurality of disparate communication links. A third communication link communicatively couples the transceiver and the telemetry device. A power source is coupled to the transceiver and to the telemetry apparatus. An operational status of at least the first and second communication links can be individually determined in real-time.

20 Claims, 12 Drawing Sheets

Related U.S. Application Data continuation of application No. 14/309,607, filed on Jun. 19, 2014, now Pat. No. 9,452,293.

(51) Int. Cl.
| | |
|---|---|
| *A61N 1/05* | (2006.01) |
| *G16H 40/63* | (2018.01) |
| *G16H 40/67* | (2018.01) |
| *A61N 1/378* | (2006.01) |

(52) U.S. Cl.
CPC ....... *A61N 1/3787* (2013.01); *A61N 1/37217* (2013.01); *A61N 1/37223* (2013.01); *A61N 1/37235* (2013.01); *G16H 40/63* (2018.01); *G16H 40/67* (2018.01)

(58) Field of Classification Search
CPC .. A61N 1/3611; A61N 1/36125; A61N 1/372; A61N 1/37217; A61N 1/37223; A61N 1/37235; A61N 1/37252; A61N 1/3787; G16H 40/63; G16H 40/67
See application file for complete search history.

(56) References Cited

U.S. PATENT DOCUMENTS

| | | | |
|---|---|---|---|
| 7,532,933 B2 | 5/2009 | Hastings et al. | |
| 7,743,151 B2 | 6/2010 | Vallapureddy et al. | |
| 7,813,806 B2 | 10/2010 | Strother et al. | |
| 7,813,809 B2* | 10/2010 | Strother | A61B 5/389 607/60 |
| 7,967,751 B2 | 6/2011 | Goscha et al. | |
| 7,978,063 B2* | 7/2011 | Baldus | A61B 5/0006 340/539.12 |
| 8,116,875 B2 | 2/2012 | Osypka et al. | |
| 8,216,135 B2 | 7/2012 | Goscha et al. | |
| 8,301,262 B2 | 10/2012 | Mi et al. | |
| 8,600,505 B2* | 12/2013 | Libbus | A61N 1/37217 607/27 |
| 8,655,451 B2* | 2/2014 | Klosterman | A61N 1/3605 607/60 |
| 9,452,293 B2* | 9/2016 | Rondoni | A61N 1/37223 |
| 10,238,878 B2* | 3/2019 | Rondoni | A61N 1/37235 |
| 2001/0051787 A1* | 12/2001 | Haller | G16H 40/40 604/66 |
| 2002/0013613 A1* | 1/2002 | Haller | A61N 1/37264 607/60 |
| 2002/0052539 A1* | 5/2002 | Haller | A61N 1/37258 600/300 |
| 2002/0072783 A1* | 6/2002 | Goedeke | A61N 1/37223 607/60 |
| 2002/0082665 A1* | 6/2002 | Haller | A61N 1/37282 607/60 |
| 2003/0144711 A1* | 7/2003 | Pless | A61B 5/0006 607/60 |
| 2003/0149459 A1* | 8/2003 | Von Arx | G16H 40/67 607/60 |
| 2004/0014486 A1* | 1/2004 | Carlton | G06Q 30/02 455/550.1 |
| 2004/0077995 A1* | 4/2004 | Ferek-Petric | A61N 1/37282 604/66 |
| 2005/0187593 A1* | 8/2005 | Housworth | A61B 5/0031 607/60 |
| 2005/0197680 A1* | 9/2005 | DelMain | A61B 5/0024 607/60 |
| 2005/0245992 A1 | 11/2005 | Persen et al. | |
| 2006/0025834 A1* | 2/2006 | Von Arx | A61N 1/37 607/60 |
| 2006/0031378 A1* | 2/2006 | Vallapureddy | A61N 1/37288 709/208 |
| 2006/0064133 A1* | 3/2006 | Von Arx | A61M 5/14276 607/17 |
| 2006/0064142 A1* | 3/2006 | Chavan | A61B 5/0031 607/60 |
| 2006/0064143 A1* | 3/2006 | Von Arx | A61M 5/14276 607/60 |
| 2006/0085039 A1 | 4/2006 | Hastings et al. | |
| 2006/0085040 A1* | 4/2006 | VanDanacker | A61N 1/37282 607/30 |
| 2006/0161213 A1* | 7/2006 | Patel | G16H 40/40 607/30 |
| 2006/0161214 A1* | 7/2006 | Patel | A61N 1/37282 607/32 |
| 2007/0067004 A1* | 3/2007 | Boveja | A61N 1/36017 607/45 |
| 2007/0135855 A1 | 6/2007 | Foshee et al. | |
| 2007/0135867 A1* | 6/2007 | Klosterman | H04L 27/02 607/60 |
| 2007/0288069 A1* | 12/2007 | Goscha | A61B 5/0031 607/60 |
| 2008/0002650 A1* | 1/2008 | Xia | H04L 47/323 370/338 |
| 2008/0132969 A1* | 6/2008 | Bennett | A61N 1/36017 607/41 |
| 2008/0154503 A1* | 6/2008 | Wittenber | A61B 5/02055 701/300 |
| 2008/0255636 A1* | 10/2008 | DelMain | A61B 5/0031 607/60 |
| 2008/0278331 A1* | 11/2008 | Hayter | A61B 5/0015 340/573.1 |
| 2008/0288024 A1* | 11/2008 | Abrahamson | H01Q 1/22 607/60 |
| 2011/0137378 A1* | 6/2011 | Klosterman | A61N 1/37217 607/60 |
| 2011/0160794 A1* | 6/2011 | Bolea | A61N 1/36139 607/42 |
| 2011/0200194 A1* | 8/2011 | Goscha | A61B 5/0031 380/286 |
| 2011/0270159 A1* | 11/2011 | Ferek-Petric | G06F 19/00 604/66 |
| 2011/0275942 A1* | 11/2011 | Stahmann | G16H 40/67 600/483 |
| 2012/0078648 A1* | 3/2012 | Reiner | G16H 40/20 705/2 |
| 2012/0083858 A1 | 4/2012 | Yamitsky | |
| 2012/0265026 A1* | 10/2012 | Shenasa | A61B 5/0006 600/301 |
| 2013/0053920 A1* | 2/2013 | LaLonde | A61N 1/3718 607/30 |
| 2013/0085550 A1* | 4/2013 | Polefko | A61N 1/3605 607/59 |
| 2013/0165819 A1* | 6/2013 | Tieu | A61B 5/0031 600/595 |
| 2013/0194106 A1* | 8/2013 | Lee | A61N 1/37252 340/870.3 |
| 2013/0314247 A1* | 11/2013 | Sicurello | H04L 1/0046 340/870.02 |
| 2014/0218211 A1* | 8/2014 | Hayter | A61B 5/746 340/870.09 |
| 2015/0119846 A1* | 4/2015 | Joglekar | A61M 5/14276 604/500 |
| 2015/0282711 A1* | 10/2015 | Thomas | A61M 5/1723 600/365 |
| 2015/0367136 A1* | 12/2015 | Rondoni | G16H 40/67 607/42 |
| 2016/0045146 A1* | 2/2016 | Fennell | A61B 5/14546 600/345 |
| 2016/0057060 A1* | 2/2016 | Fennell | G16H 40/67 370/230 |
| 2017/0007838 A1* | 1/2017 | Rondoni | A61N 1/37223 |

FOREIGN PATENT DOCUMENTS

| | | |
|---|---|---|
| WO | 2006064397 | 6/2006 |

(56) References Cited

FOREIGN PATENT DOCUMENTS

| | | |
|---|---|---|
| WO | 2013032864 | 3/2013 |
| WO | 2013112269 | 8/2013 |

OTHER PUBLICATIONS

International Search Report and Written Opinion dated Aug. 18, 2015 for PCT Application No. PCT/US2015/033197, 3 pages.
Office Action dated Dec. 19, 2017 from JP App. No. 2016-573924, 2 pages.

* cited by examiner

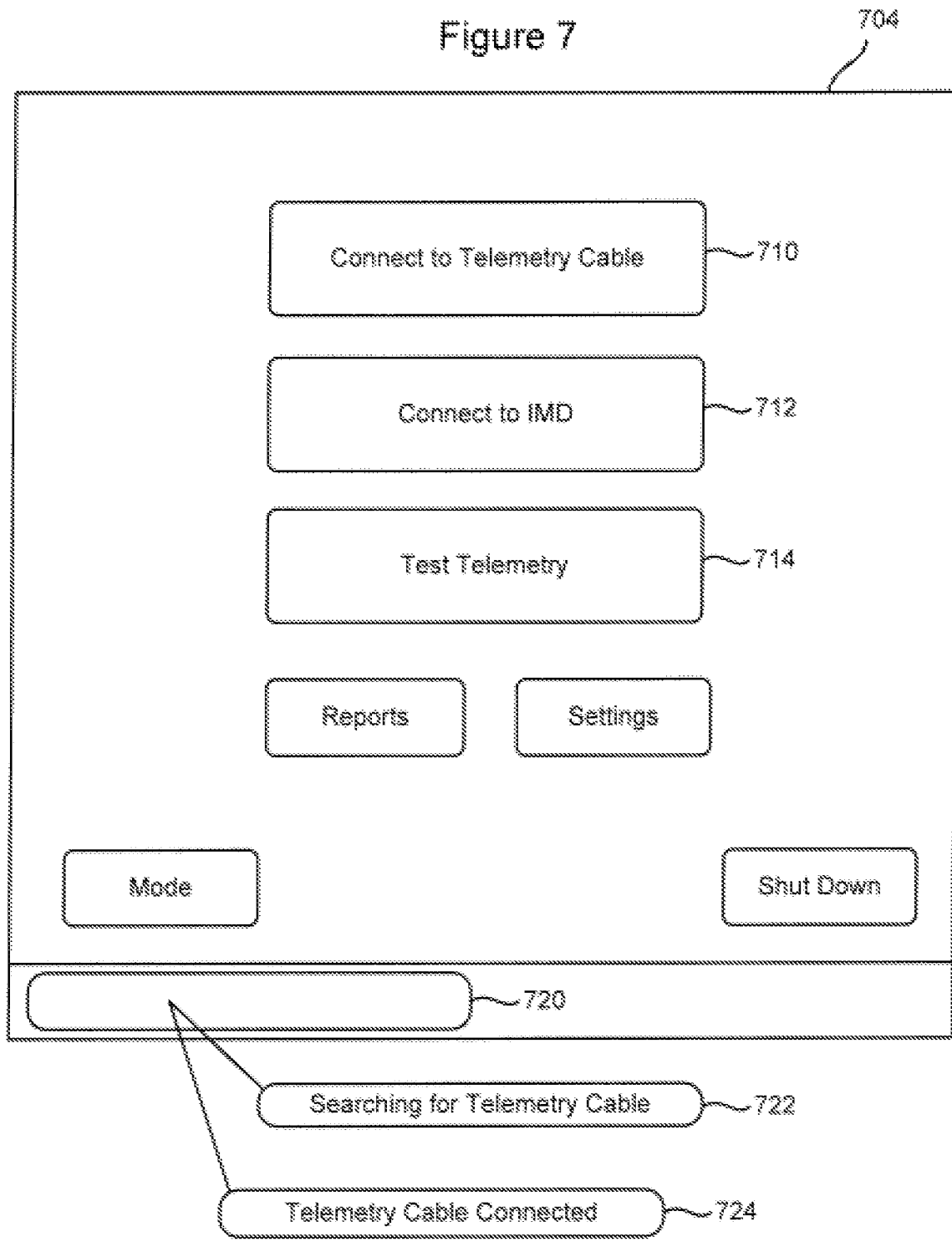

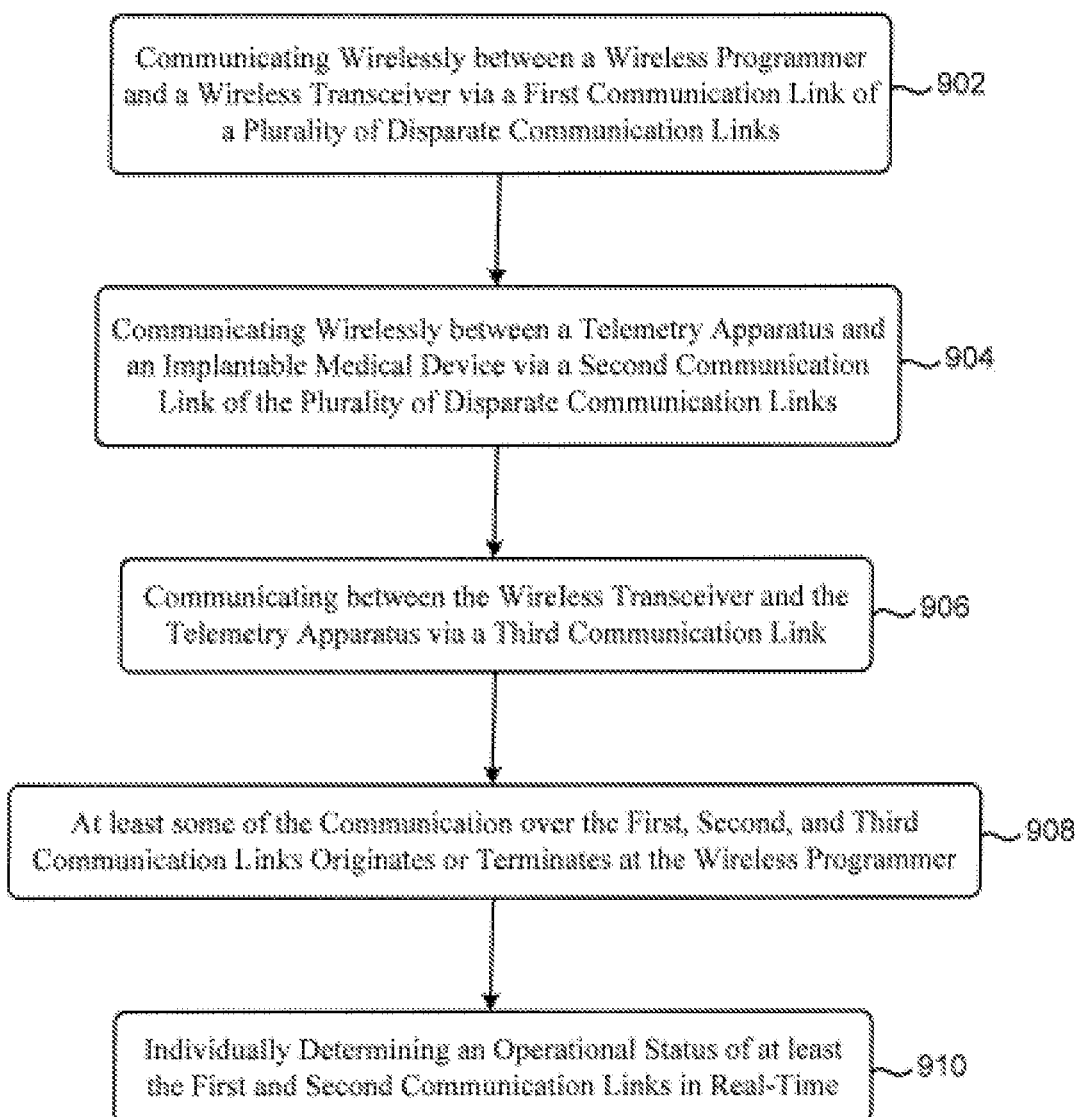

Figure 12

| THERAPY IS ON | ⏻ TURN OFF | JOHN DOE<br>ID 12345678 | DE-ID: MPLS-062 | SERIAL #: NCR___ | ◀ HOME |

ADJUST SENSING

SCREENSHOT #1 16:04

LABEL SCREENSHOT | CLEAR SELECTIONS

| SLEEP TYPE | POSITION | POLARITY | TIMING |
|---|---|---|---|
| ● AWAKE | ● SUPINE | ● INSPIRATORY UP | ● INSPIRATORY STIM |
| ○ ASLEEP | ○ RIGHT | ○ EXPIRATORY UP | ○ EXPIRATORY STIM |
| ○ ANESTHETIZED | ○ LEFT | ○ OTHER | ○ OTHER |
|  | ○ PRONE |  |  |

CANCEL    SAVE

TELEMETRY CABLE CONNECTED    BATTERY REMOVED    12 JANUARY 2014 16:05

US 11,207,531 B2

HYBRID COMMUNICATION CHANNEL FOR COMMUNICATING WITH A MEDICAL DEVICE

CROSS REFERENCE TO RELATED CASES

This is a continuation of U.S. patent application Ser. No. 15/270,136, filed Sep. 20, 2016, now U.S. Pat. No. 10,238,878, which is as continuation of U.S. patent application Ser. No. 14/309,607, filed Jun. 19, 2014, now U.S. Pat. No. 9,452,293, which are hereby incorporated by reference in their entireties.

SUMMARY

Various embodiments are directed to an apparatus and method for effecting communication between an implantable medical device (IMD) and a programmer via a communication channel. According to some embodiments, an apparatus comprises a communication channel comprising a plurality of disparate communication links configured to facilitate bi-direction communication between the IMD and the programmer. A transceiver is configured to communicate with the programmer via a first communication link of the plurality of disparate communication links. A telemetry device is configured to communicate with the IMD via a second communication link of the plurality of disparate communication links. A third communication link communicatively couples the transceiver and the telemetry device. A power source is coupled to the transceiver and to the telemetry apparatus. An operational status of at least the first and second communication links can be individually determined in real-time.

Some embodiments are directed to an apparatus and method for effecting communication between an IMD and a wireless programmer via a communication channel comprising one or more wireless communication links of differing technology. According to some embodiments, an apparatus comprises a communication channel comprising a plurality of disparate communication links configured to facilitate bi-direction communication between the IMD and the wireless programmer. A wireless transceiver is configured to wirelessly communicate with the wireless programmer via a first communication link of the plurality of disparate communication links. A telemetry device is configured to wirelessly communicate with the IMD via a second communication link of the plurality of disparate communication links. A third communication link communicatively couples the wireless transceiver and the telemetry device. A power source is coupled to the wireless transceiver and to the telemetry apparatus. An operational status of at least the first and second communication links can be individually determined in real-time.

According to further embodiments, an apparatus for effecting communication with an IMD comprises a programmer configured to interrogate and program the IMD. A telemetry apparatus comprises a communication channel comprising a plurality of disparate communication links configured to facilitate bi-direction communication between the programmer and the IMD. The telemetry apparatus also comprises a transceiver configured to communicate with the programmer via a first communication link of the plurality of disparate communication links, a telemetry device configured to communicate with the IMD via a second communication link of the plurality of disparate communication links, and a third communication link communicatively coupling the transceiver and the telemetry device. The telemetry apparatus further comprises a power source coupled to the transceiver and the telemetry apparatus. The programmer is configured to individually determine an operational status of at least the first and second communication links in real-time.

In accordance with other embodiments, an apparatus for effecting communication with an IMD comprises a wireless programmer configured to interrogate and program the IMD. A telemetry apparatus comprises a communication channel comprising a plurality of disparate communication links configured to facilitate bi-direction communication between the wireless programmer and the IMD. The telemetry apparatus also comprises a wireless transceiver configured to wirelessly communicate with the wireless programmer via a first communication link of the plurality of disparate communication links, a telemetry device configured to wirelessly communicate with the IMD via a second communication link of the plurality of disparate communication links, and a third communication link communicatively coupling the wireless transceiver and the telemetry device. The telemetry apparatus further comprises a power source coupled to the wireless transceiver and the telemetry apparatus. The wireless programmer is configured to individually determine an operational status of at least the first and second communication links in real-time.

According to some embodiments, a method for effecting communication between a programmer and an IMD involves communicating between the programmer and a transceiver via a first communication link of a plurality of disparate communication links defining a communication channel between the programmer and the IMD. The method also involves communicating between a telemetry device and the IMD via a second communication link of the plurality of disparate communication links, communicating between the transceiver and the telemetry device via a third communication link, and individually determining an operational status of at least the first and second communication links in real-time.

In accordance with other embodiments, a method for effecting communication between a wireless programmer and an IMD involves communicating wirelessly between the wireless programmer and a wireless transceiver via a first communication link of a plurality of disparate communication links defining a communication channel between the wireless programmer and the IMD. The method also involves communicating wirelessly between a telemetry device and the IMD via a second communication link of the plurality of disparate communication links, communicating between the wireless transceiver and the telemetry device via a third communication link, and individually determining an operational status of at least the first and second communication links in real-time.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 7 illustrates a display of the wireless programmer with various control buttons that can be activated as part of the testing protocol shown in FIG. 6 in accordance with various embodiments;

FIG. 9 illustrates a method for effecting communication with an IMD via a plurality of disparate communication links in accordance with various embodiments;

FIG. 12 shows an annotated respiratory waveform presented on a display of a wireless programmer in accordance with other embodiments.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
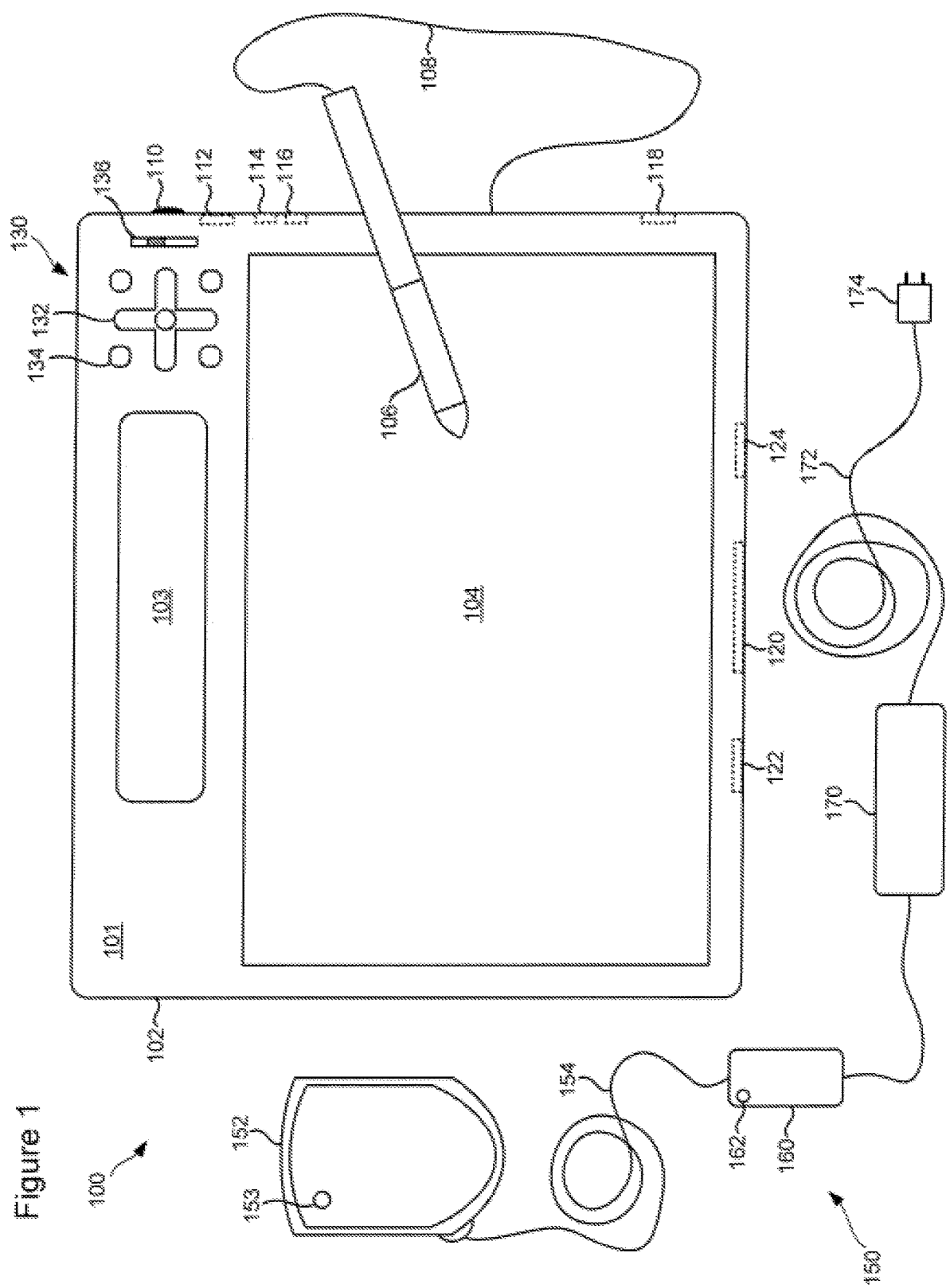
FIG. 1 shows apparatuses for effecting communication with an IMD in accordance with various embodiments.

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Embodiments of the present disclosure are directed to an apparatus and method for effecting communication between a programmer and an implantable medical device via a multiplicity of disparate communication links. Embodiments are directed to an apparatus and method for effecting communication between a programmer and an implantable medical device via a multiplicity of disparate sequential communication links, one or more of which are wireless communication links. Embodiments of the present disclosure are directed to an apparatus and method for effecting communication between a programmer and an implantable medical device via a multiplicity of disparate wireless communication links. Various embodiments are directed to an apparatus and method that provide for simultaneous monitoring of two or more disparate (e.g., sequential) wireless links that together facilitate bi-directional communication between the programmer and the IMD. Various embodiments provide for individual testing of each of the wireless links, identification as to which links are active or inactive, and successful establishment of the multi-link connection between the programmer and the IMD. Embodiments provide for real-time detection and user notification when any of the disparate wireless links is lost. Various embodiments provide for detection of signal interference (e.g., EMI) and/or signal degradation on any of the disparate wireless links. In some embodiments, the programmer is a wireless programmer, such as a tablet configured to implement an application or browser. In other embodiments, the programmer may have a wired communications interface and be configured to implement an application or browser and communicate with an IMD via a multiplicity of disparate communication links which can include one or more wired communication links.

Real-time telemetry and individual communication link feedback can be provided to a clinician via a display of the wireless programmer and on individual wireless components that support the hybrid communication link between the wireless programmer and the IMD. In some embodiments, a real-time interlock is implemented to prevent use of a down-stream communication link if an up-stream communication link is not established or is lost. One embodiment of an interlock works by disabling programmer features and controls that require communication with the IMD when one or more of the communication links between the programmer and telemetry device are unavailable. Likewise, when stable communication between the programmer and telemetry device are established, programmer features and controls requiring communication with the IMD are enabled. Certain IMD devices utilize a carrier signal that may be present regardless of communication or user operations (e.g., recharging the IMD). In this case, the IMD function interlock would trigger on a functional connection between the programmer and IMD instead of between the programmer and telemetry device. If communication is lost during an operation that requires communication with the IMD, the programmer will immediately attempt to recover those links and continue or restart the operation.

Some embodiments involve predicting communication link range and stability prior to utilization, which can be realized via a wireless indication link testing protocol that evaluates individual communication links of the hybrid connection. The link range and stability may be tested by sequentially utilizing functional links between the programmer and wireless transceiver, telemetry device, and IMD. When this test mode is operational, the programmer communicates status information concerning at least the constraining link in the system; if the link to the wireless device is not functional, the programmer will indicate this and provide instructions to improve it; likewise if the wireless link is functional but the telemetry link is not, the programmer will indicate this and provide instructions to improve the telemetry link performance. Some embodiments are directed to a hybrid communication link for increasing wireless communication range in which one of the disparate communication links consists of a connection over network infrastructure.

Various embodiments of the disclosure are directed to a telemetry apparatus, such as a telemetry cable, for effecting communication between an IMD and a wireless programmer. According to some embodiments, a communication channel comprises a plurality of disparate sequential communication links configured to facilitate bi-direction communication between the IMD and the wireless programmer. A wireless transceiver is configured to wirelessly communicate with the wireless programmer via a first communication link of the plurality of disparate communication links. A telemetry device is configured to wirelessly communicate with the IMD via a second communication link of the plurality of disparate communication links. The wireless transceiver and the telemetry device are communicatively coupled via a third communication link. A power source is coupled to the wireless transceiver and to the telemetry apparatus. An operational status of at least the first and second communication links can be individually determined in real-time. The apparatus may be configured for operation only with a particular wireless programmer to which the apparatus is paired. Other embodiments of the disclosure are directed to a system comprising a wireless programmer and a telemetry apparatus of a type described herein.

FIG. 1 shows apparatuses for effecting communication with an implantable medical device in accordance with various embodiments. Some embodiments are directed to a telemetry cable 150 configured to effect communication between an IMD and a wireless programmer 102. Other embodiments are directed to a system comprising the wireless programmer 102 and the telemetry cable 150. FIG. 1 shows a wireless programmer 102 configured to communicate with a telemetry cable 150. According to various embodiments, the wireless programmer 102 can be implemented as a tablet computer or other mobile computing device (e.g., a notebook or laptop). The wireless programmer 102 is configured to implement an application (also referred to as an "app") or a browser that facilitates clinician interaction with the telemetry cable 150 and the IMD. The wireless programmer 102 can be used by a clinician to interrogate an IMD and make adjustments to various parameters of an IMD (referred to as "programming" the IMD), monitor therapy delivered by the IMD, and monitor patient adherence to prescribed therapy. The telemetry cable 150 communicates wirelessly with the IMD and facilitates wireless communication between the IMD and the wireless programmer 102. Generally, each wireless programmer 102 is uniquely paired to a particular telemetry cable 150, and each wireless programmer 102 works only with its uniquely paired telemetry cable 150. In some embodiments, a generic portable computing device (e.g., a tablet or laptop) can be configured by software to serve as an "app-based" programmer, and can operate as a stand-alone programmer or in cooperation with a desktop or stationary programmer (e.g., PC programmer). App-based programmers can be uniquely paired to a particular telemetry cable at any given moment, but this pairing relationship can be changed on-the-fly as a sleep technician moves from his or her PC terminal to a tablet and for utilization by remote support individuals.

The wireless programmer 102 includes a display 104 and a stylus 106 which allows the clinician to interact with the display 104, such as by inputting, modifying, and reviewing data. The stylus 106 may be a double sided device, so that either the pen tip or the eraser site may be used. The stylus 106 is shown tethered to the programmer 102 via a cable 108, which provides signaling and power to the stylus 106. Alternatively, the stylus 106 may be a wireless device with its own power source, such as a battery. In some embodiments, the display 104 can be configured as a touchscreen, in which case the stylus 106 may be excluded or an optional accessory. A handle 103 is provided in the upper portion of the programmer 102, and a recessed section of the programmer housing 101 above or below the handle 103 can be used to store the stylus 106 when not in use.

The wireless programmer 102 includes a number of interfaces, buttons, and controls, several of which are shown in the illustrative embodiment of FIG. 1. A power button 110 is provided on an upper right edge of the housing 101, and a cluster of controls 130 is provided on an upper right portion of the front surface of the housing 102. The control cluster 130 includes a multi-position control 132 that allows the clinician to interact with the processor and display 104 of the programmer 102 in various ways. Additional buttons 134 can be situated proximate (or apart from) the control cluster 130. For example, the control cluster 130 and additional buttons 134 can allow the clinician to select between different operating modes and/or various user-assignable or emergency-off functions (e.g., places the IMD into a known safe state or performs live-saving functions). To the right of the control cluster 130 is a dimmer switch 136 configured to allow the clinician to easily adjust the brightness of the display 104 and/or illuminated control buttons as the clinician moves between rooms of varying ambient light intensity (e.g., a relatively dim patient room vs. a relatively bright clinician room). The wireless programmer 102 includes a number of different interfaces/component including a fingerprint/biometric ID reader 112, a lock button 114 to restrict access, a camera button for taking pictures 116, a power connector plus USB port 118, a network cable and USB port 120, a speaker 122, and a microphone 124 (which could be located on the front surface of the programmer housing. The interfaces and components listed above are for purposes of illustration, not of limitation.

The telemetry cable 150 is configured to wirelessly communicate with both the wireless programmer 102 and an IMD. The telemetry cable 150 effectively serves as a wireless bridge or modem between the programmer 102 and the IMD. The telemetry cable 150 comprises disparate communication devices that together support a communication channel comprising disparate sequential communication links configured to facilitate bidirectional communication between the IMD and the wireless programmer 102. In particular, the telemetry cable 150 provides for bi-directional communication with the IMD and bi-directional communication with the wireless programmer 102. According to various embodiments, the wireless programmer 102 monitors for establishment of, and loss of connectivity with, each of the disparate communication links that define the hybrid communication channel. In some embodiments, the telemetry cable 150 is configured to self-monitor its connectivity with the wireless programmer 102 and to indicate a status of said connectivity. In some embodiments, the telemetry cable 150 is configured to deliver power to the IMD in addition to communicating with it (e.g., via inductive coupling). The IMD may use the wireless power to operate a portion or all of its functions or to recharge the IMD battery or capacitor.

In accordance with the embodiment shown in FIG. 1, the telemetry cable 150 includes a telemetry head 152 configured to wirelessly communicate with the IMD via a near-field link. The telemetry head 152 is shown to include a status indicator 153, such as an LED indicator. The telemetry head 152 can be configured to self-monitor establishment and loss of connectivity with the wireless programmer 102. Alternatively, or in addition, the telemetry head 152 can be configured to self-monitor establishment and loss of connectivity with the IMD. For example, the status indicator 153 can be illuminated with a green color to indicate good signaling between the telemetry head 152 and the IMD. The status indicator 153 can be illuminated with an orange color to indicate poor or no signaling between the telemetry head 152 and the IMD.

In some embodiments, the telemetry head 152 is configured to inductively communicate with the IMD via a near-field link. A near-field link appropriate for effecting communications with an IMD typically has a range of about 5 centimeters. A typical inductive near-field link between the telemetry head 152 is highly directional, operates safely through human tissue, and is susceptible to electrical noise. In addition to being extremely short range, inductive telemetry communication is low-power and does not interfere with medical or communication equipment. However, inductive telemetry signals are susceptible to electrical noise, such as from hospital beds, smart phones, tube monitors/TVs, power supplies, respiratory inductive plethysmography (RIP), RIP belts, the RIP box, PSG wires, and the head box, for example. In some embodiments, an alternative to near-field inductive communication can be implemented, including: e-field communications (MICS, ISM), and medium range induction technology which utilizes advanced amplifiers and transmitters to achieve ranges of up to 1 m. It is noted that the use of multiple coils, such as in three-axes implementations, can eliminate the directionality issue with inductive links.

A cable 154 extends from the telemetry head 152 and is connected to a wireless transceiver 160. The wireless transceiver 160 may be configured for short-range radio frequency (RF) communication. For example, the wireless transceiver 160 may be configured to implement a short-range RF communication link, such as by implementing a Bluetooth® (short-wavelength UHF radio waves in the ISM band from 2.4 to 2.485 GHz) or ZigBee® (radio waves in ISM radio bands: 868 MHz in Europe, 915 MHz in the USA and Australia, and 2.4 GHz in most jurisdictions worldwide) communications protocol. In some embodiments, the wireless transceiver 160 can be configured to wirelessly communicate with existing network infrastructure via an appropriate RF communication protocol, such as Wi-Fi® (also considered a short-range RF communication link of up to about 45 meters indoors). In such embodiments, a hybrid communication link can be established between the IMD and the wireless programmer 102 using a wireless local area network (WLAN) via a wireless network connection for increasing the wireless communication range of the telemetry cable 150.

The wireless transceiver 160 typically has a range significantly greater than that of the link established by the telemetry head 152 (e.g., on the order of at least a magnitude difference). For example, the wireless transceiver 160 may have a range of about 5-20 meters. In contrast to the near-field link described above, a typical wireless link established between the wireless transceiver 160 and wireless programmer 102 is not directional and is blocked by human tissue. Moreover, a wireless transceiver 160 implemented according to a Bluetooth® protocol operates at the same frequencies as Wi-Fi® and is ubiquitous and safe for use in hospitals and care facilities.

The wireless transceiver 160 is shown to include a status indicator 162. The wireless transceiver 160 can be configured to self-monitor establishment and loss of connectivity with the wireless programmer 102. Alternatively, or in addition, the wireless transceiver 160 can be configured to self-monitor establishment and loss of connectivity with the telemetry head 152. In some implementations, the status indicator 162 includes an LED, which indicates a good or nominal operating status by way of constant LED illumination. The status indicator 162 may blink or be extinguished to indicate a poor or non-operating status of the wireless transceiver 160. Power is supplied to the telemetry cable 150 by way of a power supply 170, which is shown to include a power cable 172 terminated by a standard AC wall plug 174. The power supply 170 provides power for both the wireless transceiver 160 and the telemetry head 152.

Figure 2:
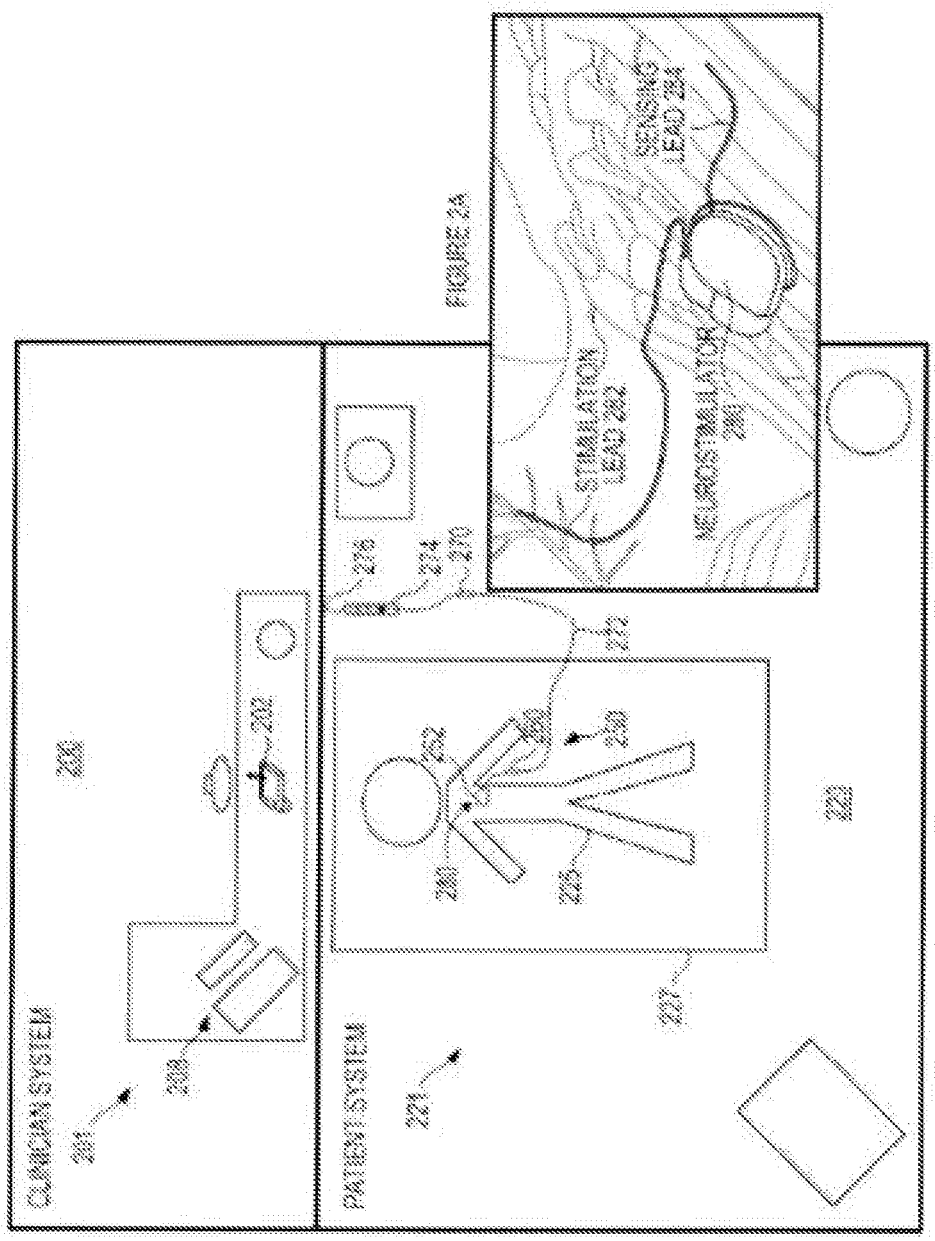
FIG. 2 is an illustration of a clinic or hospital equipped to monitor a patient during a medical evaluation, such as a sleep study for determining whether the patient is suffering from a sleep disorder, in accordance with various embodiments.

FIG. 2 is an illustration of clinic or hospital rooms equipped to monitor a patient 225 during a medical evaluation, such as a sleep study for determining whether the patient is suffering from a sleep disorder. In this illustrative embodiment, a neurostimulator 280 (see also FIG. 2A) has been implanted in the patient 225 in the subclavian region for purposes of treating obstructive sleep apnea. Obstructive sleep apnea is a common disorder, characterized by recurrent narrowing and closure of the upper airway accompanied by intermittent oxyhemoglobin desaturation and sympathetic activation. The onset of apnea is accompanied by a reduction in drive to the upper-airway muscles, and upper-airway patency is strongly correlated with the activation of the genioglossus muscle. Upper-airway stimulation with the use of unilateral stimulation of the hypoglossal nerve, synchronous with ventilation, is a viable treatment option, providing significant and clinically meaningful reductions in the severity of obstructive sleep apnea and self-reported sleepiness and improvements in quality-of-life measures.

The neurostimulator 280 shown in FIG. 2 includes a stimulation lead 282 that extends from the housing of the neurostimulator 280 to the hypoglossal nerve in the patient's neck. A sensing lead 284 extends from the housing of the neurostimulator 280 and is implanted at an intercostal muscle location of the rib cage. The sensing lead 284 detects intercostal muscle movement during patient respiration, signals from which are used to detect patient respiration. A pulse generator in the neurostimulator 280 provides electrical stimulation to the hypoglossal nerve via the stimulation lead 282 based on detected patient respiration.

In the illustrative testing environment shown in FIG. 2, the patient 225 is shown lying down on a bed 227 in a patient room 220 for purposes of conducting a sleep study. The patient room 220 may be configured and decorated much like a typical motel room to simulate a restful bedroom environment. FIG. 2 also shows a clinician room 200 which is typically a separate room adjacent to or near the patient room 220. The clinician room 200 is typically close to the patient room 220 to facilitate efficient evaluation of, and communication with, the patient 225 during the sleep study. Importantly, the clinician room 200 is separated by a wall or other privacy structure that provides a measure of privacy and security for the patient 225 during the sleep study. Although the presence of a walled structure between the clinician and patient rooms 200 and 220 advances the objective of enhancing the sleep environment for the patient's benefit, the walled structure presents a physical barrier between diagnostic equipment distributed between the physically separate clinician and patient rooms 200 and 220.

In the illustrative embodiment shown in FIG. 2, a patient system 221 is situated in the patient room 220 and a clinician system 201 is situated in the clinician room 200. The patient system 221 includes a telemetry cable 250 positioned proximate the patient 225, and includes a telemetry head 252 communicatively coupled to a wireless transceiver 260. The telemetry cable 250 is connected to a power supply 270 via a power cable 272. The power supply 270 is shown connected to a AC power strip 274 which, in turn, is electrically connected to a standard AC wall socket 276. The clinician system 201 includes a wireless programmer 202, which is shown resting on a work desk within the clinician room 200. A computer system 208 and other equipment may be provided in the clinician room 200. The wireless programmer 202 situated within the clinician room 200 is communicatively coupled to the neurostimulator 280 via the telemetry cable 250. The wireless programmer 202 can be used by a clinician to interact with the neurostimulator 280 without disturbing the patient's sleep, which is important for conducting productive sleep studies.

Figure 3:
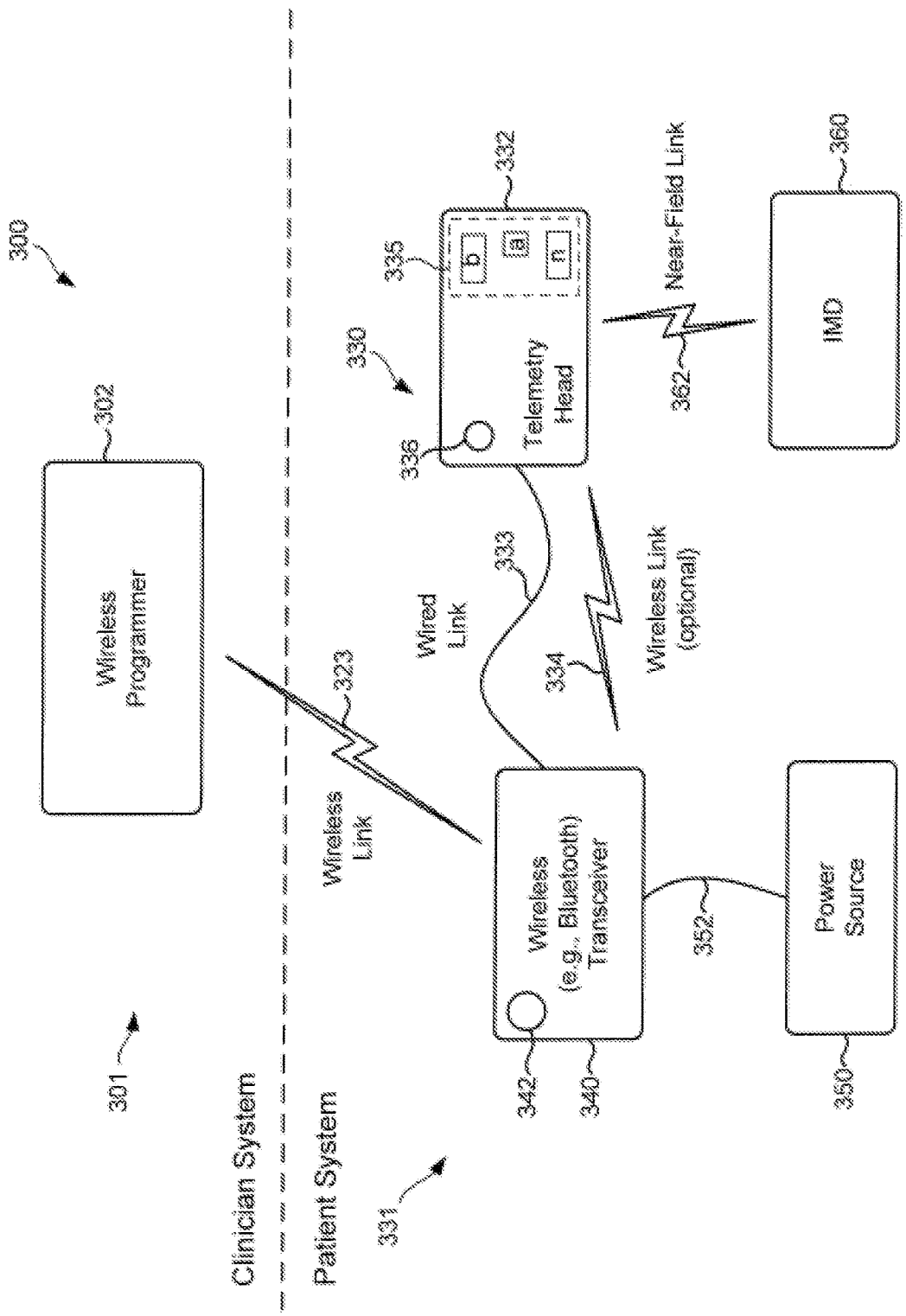
FIG. 3 illustrates an apparatus for effecting communication with an IMD in accordance with various embodiments.

FIG. 3 illustrates an apparatus for effecting communication with an IMD in accordance with various embodiments. In the embodiment illustrated in FIG. 3, the apparatus 300 includes a wireless programmer 302 configured to communicate with an IMD 360, such as a neurostimulator for treating obstructive sleep apnea, via a wireless communication channel comprising disparate communication links, including a wireless link 323 and a near-field link 362. The wireless programmer 302 is illustrated as a component of the clinician system 301 that can be operated from a room adjacent to or near a room within which a patient system 331 is situated. The patient system 331 includes a telemetry cable 330 having a telemetry head 332 communicatively coupled to a wireless transceiver 340, such as a Bluetooth® or ZigBee® transceiver. The telemetry head 332 communicates with the IMD 360 via a separate wireless link, shown as a near-field link 362. In some implementations, the near-field link 362 can be an inductive communication link.

In one implementation, a wired link 333 communicatively couples the telemetry head 332 with the wireless transceiver 340. In other implementations, a wireless link 334 can be implemented to communicatively couple the telemetry head 332 with the wireless transceiver 340. The telemetry head 332 can include a status indicator 336, which provides a visual indication of the operating status of the telemetry head 332. The telemetry head 332 can include a user control facility 335 to allow user adjustment of one or more telemetry device functions. According to some embodiments, the user control facility 335 allows the clinician to control basic operations of the telemetry device 332 without need of the full programmer interface. Utilization of these controls 335 includes allowing a clinician quick access to basic controls of the telemetry device 332 when in the patient's room, as well as allowing the same control of the telemetry device 332 by the patient in some embodiments. For example, the user control facility 335 may include a number of control buttons (e.g., buttons a-n) that are actuatable by the clinician and control various basic operations of the telemetry device 332. Button 335-a, for example, can be an on/off switch that respectively enables and disables manual adjustment of one or more functions of the telemetry device 332. Button 335-b can be a variable rocker switch that allows the clinician to gradually (e.g., step-wise) increase and decrease the strength of the wireless (e.g., inductive) link between the telemetry device 332 and the implantable medical device 360. Button 335-n can be a switch that initiates a self-diagnostic test that assesses the present ability of the telemetry device 332 to communicatively interface with the IMD 360. Other buttons may be provided to effectuate desired operations and/or functionality. For example, button 335-n can be an emergency button that places the IMD 360 into a known safe mode or causes the IMD 360 to perform a life-saving function. The emergency button 335-n may, for example, turn a neurostimulator off, return a pacemaker to a basic mode, or disable a defibrillation capability of an ICD (implantable cardioverter/defibrillator).

The wireless transceiver 340 can include a status indicator 342, which provides a visual indication of the operating status of the transceiver 340. A power source 350 is shown coupled to the wireless transceiver 340 via a wired power cable 352. The power source 530 provides power to both the wireless transceiver 340, via the power cable 352, and to the telemetry head 332, via the wired link 333. In some implementations, the power source 350 is configured to connect with a standard AC wall socket. In other implementations, the power source 350 may be a battery or other self-contained power source. In implementations that use a wireless link 334 between the telemetry head 332 and wireless transceiver 340, the telemetry head 332 may include its own power source, such as a battery.

Figure 4:
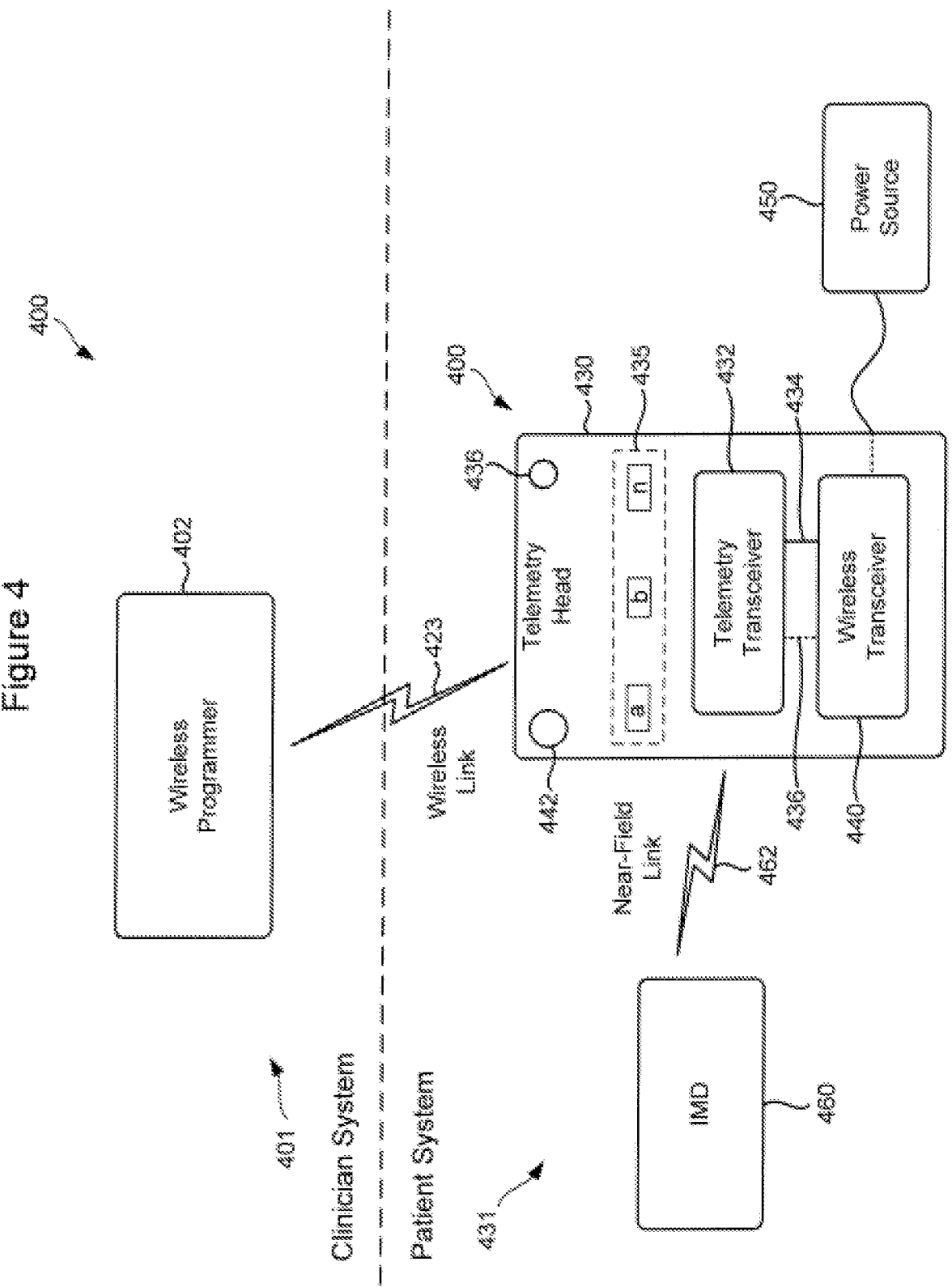
FIG. 4 illustrates an apparatus for effecting communication with an IMD in accordance with various embodiments.

FIG. 4 illustrates an apparatus for effecting communication with an IMD in accordance with various embodiments. In the embodiment illustrated in FIG. 4, the apparatus 400 includes a wireless programmer 402 configured to communicate with an IMD 460 (e.g., a neurostimulator for treating obstructive sleep apnea) via a wireless communication channel comprising disparate communication links, including a wireless link 423 and a near-field link 462. The wireless programmer 402 is illustrated as a component of the clinician system 401 that can be operated from a room adjacent to or near a room within which a patient system 431 is situated. In the embodiment shown in FIG. 4, the patient system 331 includes a telemetry device or apparatus 400 configured to wirelessly communicate with both the wireless programmer 402 and the IMD 460 using different wireless communication links. The telemetry device 400 shown in FIG. 4 integrates into a single device a telemetry transceiver 432 and a wireless transceiver 440.

The telemetry transceiver 432 is configured to establish a near-field wireless link 462 with the IMD 460. The wireless transceiver 440 is configured to establish a short range RF communication link with the wireless programmer 402 (e.g., via a Bluetooth® or ZigBee® protocol). The wireless transceiver 440 is communicatively coupled to the telemetry transceiver 432 via a signaling channel 434. In one implementation, a power connection 436 couples power supplied by a power source 450 from the wireless transceiver 440 to the telemetry transceiver 432. In another implementation, the power source 450 supplies power to the wireless transceiver 440 and the telemetry transceiver 432 individually. According to some embodiments, the telemetry transceiver 432 and the wireless transceiver 440 constitute discrete components of the telemetry device 400. In other embodiments, the telemetry transceiver 432 and the wireless transceiver 440 are implemented as components of a common integrated circuit or otherwise populating a common printed circuit board, with conductive traces provided for communicating data signals and power thereto and/or therebetween.

The telemetry device or apparatus 400 can include a user control facility 435 to allow user adjustment of one or more telemetry device functions. According to some embodiments, the user control facility 435 allows the clinician to control basic operations of the telemetry device 432 without need of the full capabilities of the programmer 402. As was previously discussed, utilization of these controls 435 includes allowing a clinician quick access to basic controls of the telemetry device 432 when in the patient's room, as well as allowing the same control of the telemetry device 432 by the patient in some embodiments. For example, the user control facility 435 may include a number of control buttons (e.g., buttons a-n) that are actuatable by the clinician and control various basic operations of the telemetry device 432. Buttons 435-a, 435-b, and 435-n, for example, can have the same or different functionality as described above with reference to controls 335a-n shown in FIG. 3. Other buttons may be provided to effectuate desired operations and/or functionality.

Figure 5:
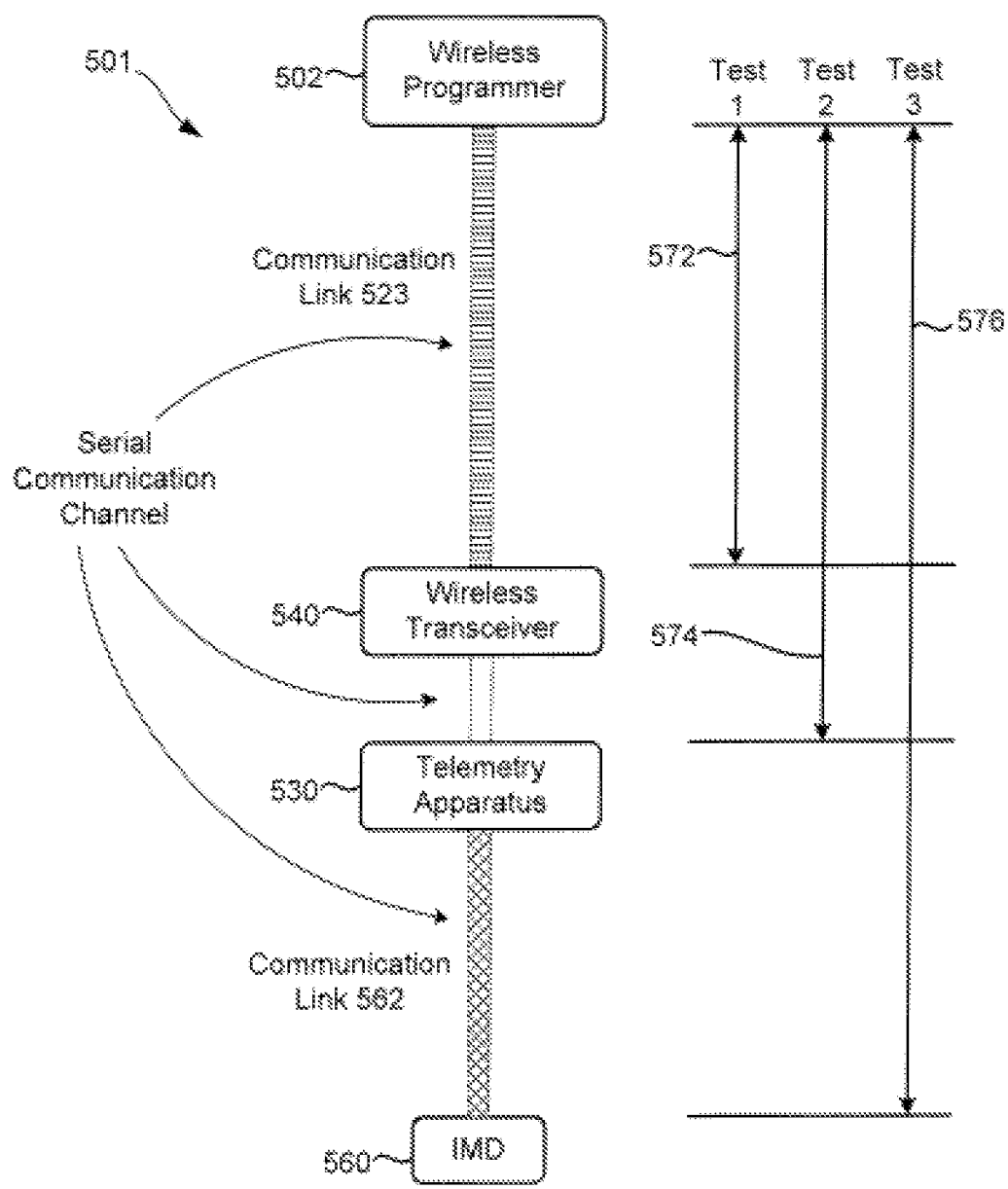
FIG. 5 illustrates a testing protocol for determining the operational status of various components of a communication channel comprising disparate communication links configured to facilitate bi-directional communication between an IMD and a wireless programmer in accordance with various embodiments.

FIG. 5 illustrates a testing protocol for determining the operational status of various components of a communication channel comprising disparate sequential communication links configured to facilitate bi-directional communication between an IMD and a wireless programmer in accordance with various embodiments. According to the embodiment shown in FIG. 5, a communication channel established between a wireless programmer 502 and an IMD 560 includes various components of a telemetry cable 501. The telemetry cable 501 includes a wireless transceiver 540 configured to establish a communication link 523 of a first type with respect to the wireless programmer 502. The telemetry cable 501 further includes a telemetry apparatus 530 configured to establish a communication link 562 of a second type with respect to the IMD 560. The two communication links 523 and 562 can differ in terms of one or more of protocol, technology, range, interference characteristics, or other attributes discussed herein. For example, the communication link 562 can have a short range, on the order of centimeters for example, and be capable of transmission through human tissue. The communication link 523 can have a long range relative to the communication link 562 (e.g., on the order of meters), and capable of passing through structural walls within a building.

According to the testing protocol shown in FIG. 5, the operational status of each component of the communication channel established between the wireless programmer 502 and IMD 560 can be tested. Testing the operational status of the wireless transceiver 540 can involve passing signals between the wireless programmer 502 and the wireless transceiver 540, and determining the viability of the communication link 523 based on this signaling. After determining the viability of communication link 523, testing the operational status of the telemetry apparatus 530 can involve passing signals between the wireless programmer 502 and the telemetry apparatus 530 via the communication link 523 and a wired or wireless connection between the wireless transceiver 540 and telemetry apparatus 530, and determining the viability of the communication link therebetween. Testing the operational status of the IMD 560 can involve passing signals between the wireless programmer 502 and the IMD 560 via the wireless transceiver 540, telemetry apparatus 530, and communication links 523 and 562, and determining the viability of the communication link therebetween.

Figure 6:
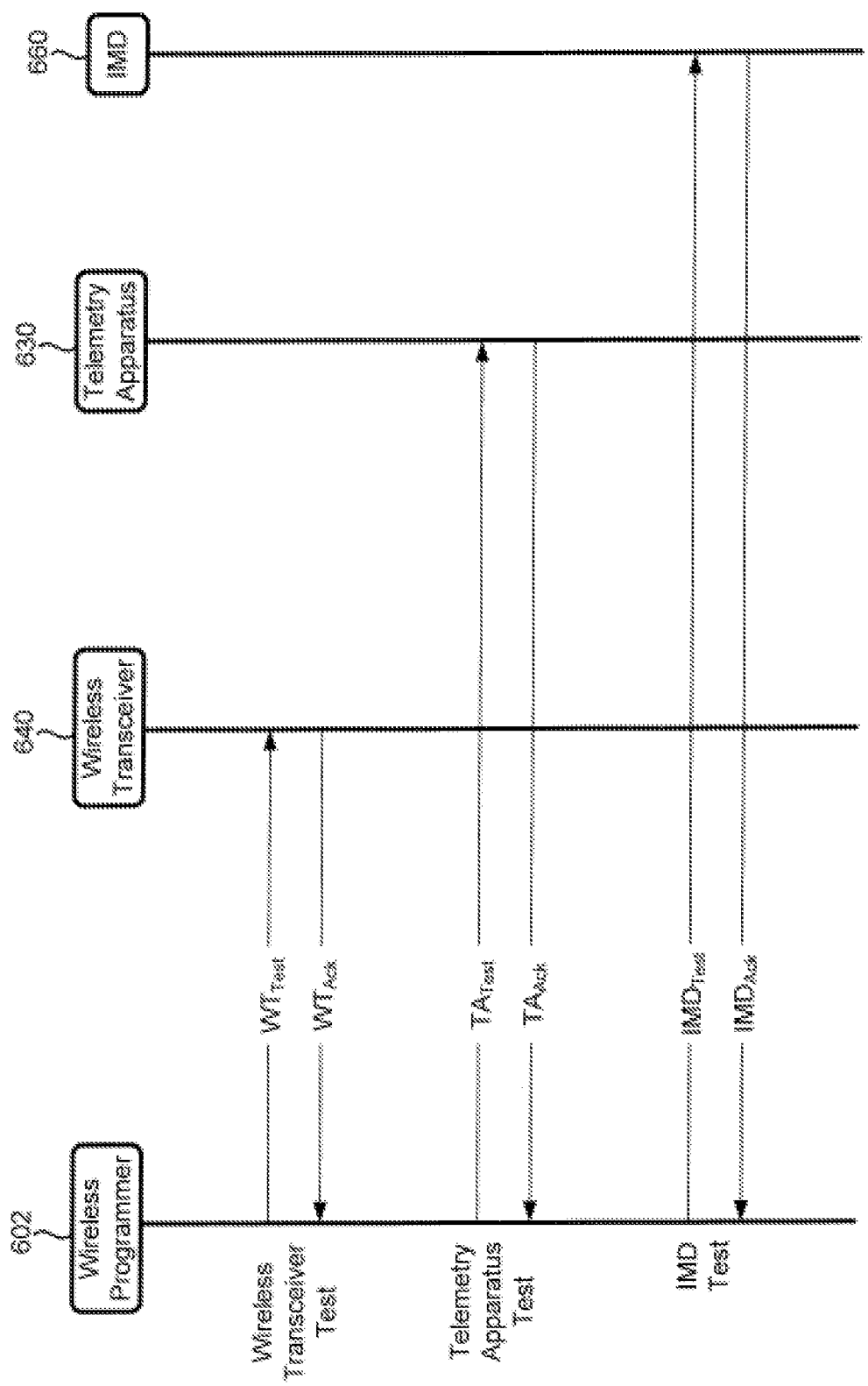
FIG. 6 illustrates a testing protocol for determining the operational status of various components of the communication channel comprising disparate communication links configured to facilitate bi-directional communication between an IMD and a wireless programmer in accordance with other embodiments.

FIG. 6 illustrates a testing protocol for determining the operational status of various components of the communication channel comprising disparate sequential communication links configured to facilitate bi-directional communication between an IMD and a wireless programmer in accordance with other embodiments. FIG. 7 illustrates a display 704 of the wireless programmer with various control buttons that can be activated as part of the testing protocol shown in FIG. 6. As a shown in FIG. 7, a button 710 for establishing connection with the telemetry cable can be activated by the clinician, such as by use of a stylus. Establishing connection with the telemetry cable involves searching, by the wireless programmer, for the telemetry cable using a signaling protocol (e.g., wireless handshake protocol). The status of this search is indicated by a status message 722, which can be presented in status window 720 on the display 704.

Figure 8A:
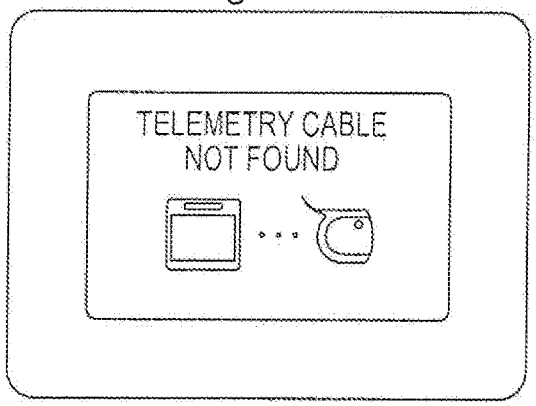
FIGS. 8A-8F are messages concerning the status of various communication links presented on a display of a wireless programmer in accordance with various embodiments.

Searching for the telemetry cable can involve the wireless transceiver test protocol shown in FIG. 6, in which a test signal, $WT_{TEST}$, is generated by the wireless programmer 602 and transmitting to the wireless transceiver 640. If operating properly, the wireless transceiver 640 generates an acknowledgment signal, $WT_{ACK}$, which is transmitted back to the wireless programmer 602. In addition to generating the acknowledgment signal, $WT_{ACK}$, the wireless transceiver 640 can illuminate a status indicator, such as an LED. In response to receiving the acknowledgment signal, $WT_{ACK}$, the wireless programmer 602 displays an indication of the operating status of the wireless connection between the wireless programmer 602 and the wireless transceiver 640, such as by presentation of a "Telemetry Cable Connected" message 724 in the status window 720. If an acknowledgment signal, $WT_{ACK}$, is not received, the wireless programmer 602 displays a message, such as that shown in FIG. 8A, that the telemetry cable cannot be found. Suggestions for remedying the problem can be displayed (e.g., "Confirm Telemetry Cable is Plugged In"). It is noted that button 710 can be an optional button, and that searching for the telemetry cable can be initiated upon selecting an operating mode involving the telemetry cable.

After determining that the telemetry cable is connected and that the wireless transceiver 640 is operating properly, the connection between the wireless programmer 602 and the telemetry apparatus 630 can be tested. A telemetry apparatus test, such as that shown in FIG. 6, can be initiated in response to actuation of button 710 (Connect to Telemetry Cable) or button 712 (Connect to IMD), depending on the operating system software of the programmer 602. According to the telemetry apparatus test shown in FIG. 6, the wireless programmer 602 generates a test signal, $TA_{TEST}$, which is transmitted to the wireless transceiver 640 and then onto the telemetry apparatus 630. In response to receiving the test signal, $TA_{TEST}$, the telemetry apparatus 630 generates an acknowledgment signal, $TA_{ACK}$, which is transmitted back to the wireless programmer 602 via the wireless transceiver 640. In response to receiving the acknowledgment signal, $TA_{ACK}$, the wireless programmer 602 may be configured to display a message in the status window 720 indicating that the telemetry apparatus 630 is operating properly (e.g., maintaining the "Telemetry Cable Connected" message 724 in the status window 720). The status indicator on the telemetry apparatus 630 (e.g., telemetry head) can be illuminated indicating successful connection with the telemetry apparatus 630. If the acknowledgment signal, $TA_{ACK}$, is not received, the wireless programmer 602 displays a message, such as one similar to that shown in FIG. 8A, that the telemetry apparatus (e.g., telemetry head) is not responsive. Suggestions for remedying the problem can be displayed. If physically coupled, $TA_{TEST}$ could be used to determine the status of the connection to the wireless transceiver 640 and telemetry apparatus 630 simultaneously. If $TA_{ACK}$ is not received, the wireless programmer 602 would indicate that the telemetry cable could not be found due to lack of the wireless connection to the wireless transceiver 640 and an appropriate message would be displayed.

Figure 8B:
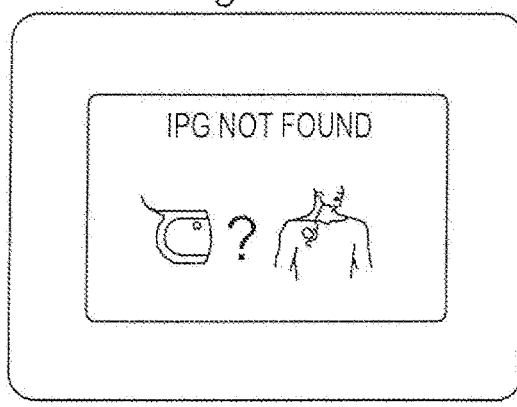
Figure 8C:
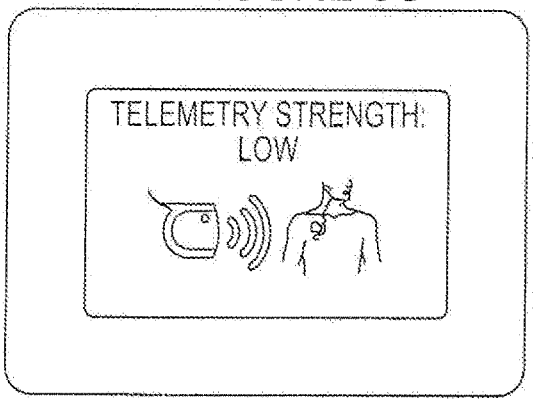
Figure 8D:
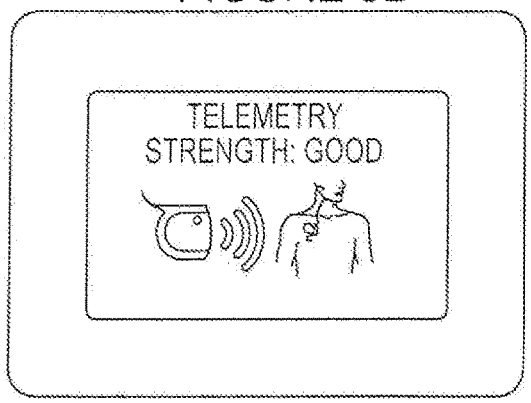
Figure 8E:
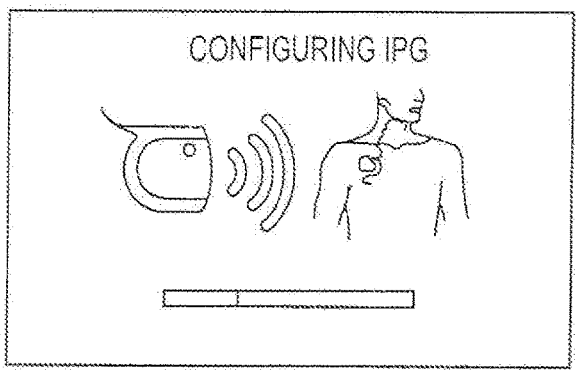
Figure 8F:
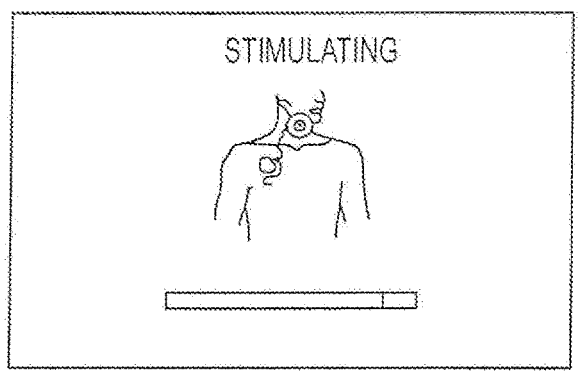

After determining that the telemetry cable is connected and operating properly, a test can be performed to determine if the IMD 660 is responsive to commands issued by the wireless programmer 602. An IMD test can be initiated, such as by actuating a Test Telemetry button 714 presented on the display 704 shown in FIG. 7. In response to actuating button 714, the IMD test shown in FIG. 6 can be initiated, in which the wireless programmer 602 transmits a test signal, $IMD_{TEST}$, to the IMD 660 via the wireless transceiver 640 and telemetry apparatus 630. The IMD test signal can cause the IMD 660 to generate an acknowledgment signal, $IMD_{ACK}$, indicating that the IMD 660 is responsive to interrogation and/or programming (e.g., establishing or modifying one or more IMD parameters) by the wireless programmer 602. If an acknowledgment signal, $IMD_{ACK}$, is not received, the wireless programmer 602 displays a message, such as that shown in FIG. 8B, that the IMD (e.g., implantable pulse generator or IPG) cannot be found. Suggestions for remedying the problem can be displayed (e.g., reposition the telemetry head over the IPG or remove the source of signal interference). After confirming that a communication link has been successfully established between the wireless programmer 602 and the IMD 660, the quality of the near-field communication link between the telemetry apparatus 640 and the IMD 660 can be tested, and the results of the testing displayed on the programmer's display (e.g., Telemetry Strength: LOW (FIG. 8C); Telemetry Strength: GOOD (FIG. 8D)). The display of the wireless programmer 602 can provide direct feedback when configuring new IMD parameters and provides insight for troubleshooting telemetry problems (e.g., Configuring IPG (FIG. 8E); Stimulating (FIG. 8F)).

According to some embodiments, a real-time interlock can be implemented by the wireless programmer 602 to prevent use of a down-stream communication link if an up-stream communication link is not established or is lost. For example, the programmer 602 can be configured to prevent use of the telemetry apparatus 630 in response to determining that the connection with the wireless transceiver 640 is lost or unstable. In another example, the programmer 602 can be configured to prevent interrogation or programming of the IMD 660 in response to detecting loss or instability of any of the communication links between the telemetry apparatus 630, wireless transceiver 640, and wireless programmer 602. The interlock can be deactivated in response to testing and confirming the operational status of each disparate communication link of the connection between the wireless programmer 602 and IMD 660.

FIG. 9 illustrates a method for effecting communication with an IMD via a plurality of disparate sequential communication links in accordance with various embodiments. In particular, FIG. 9 illustrates a method for communicating wirelessly between the wireless programmer and an IMD via a communication channel comprising a plurality of disparate communication links. The method involves communicating 902 wirelessly between the wireless programmer and a wireless transceiver via a first communication link of the plurality of disparate communication links. The method shown in FIG. 9 also involves communicating 904 wirelessly between a telemetry apparatus and the IMD via a second communication link of the plurality of disparate communication links. The method further involves communicating 906 between the wireless transceiver and the telemetry apparatus via a third communication link. The third communication link can be a wired conductor or a wireless link. In some embodiments, the third communication link can be one or more conductive traces of an integrated circuit or printed circuit board. At least some of the communication over the first, second, and third communication links originates or terminates 908 at the wireless programmer. The method also involves individually determining 910 an operational status of at least the first and second communication links in real-time.

The methodology shown in FIG. 9 may involve other processes, such as supplying power to the wireless transceiver, transmitting power from the wireless transceiver to the telemetry device via the third communication link, and transmitting data signals between the wireless transceiver and the telemetry device via the third communication link. The methodology shown in FIG. 9 may also involve self-monitoring connectivity with the wireless programmer by each of the wireless transceiver and the telemetry device, and indicating a connectivity status by each of the wireless transceiver and the telemetry device. The methodology shown in FIG. 9 can involve self-monitoring connectivity with the implantable medical device by the telemetry device, and indicating a connectivity status by the telemetry device. The methodology shown in FIG. 9 may further involve preventing use of the second communication link in response to loss or non-establishment of the first communication link.

Figure 10:
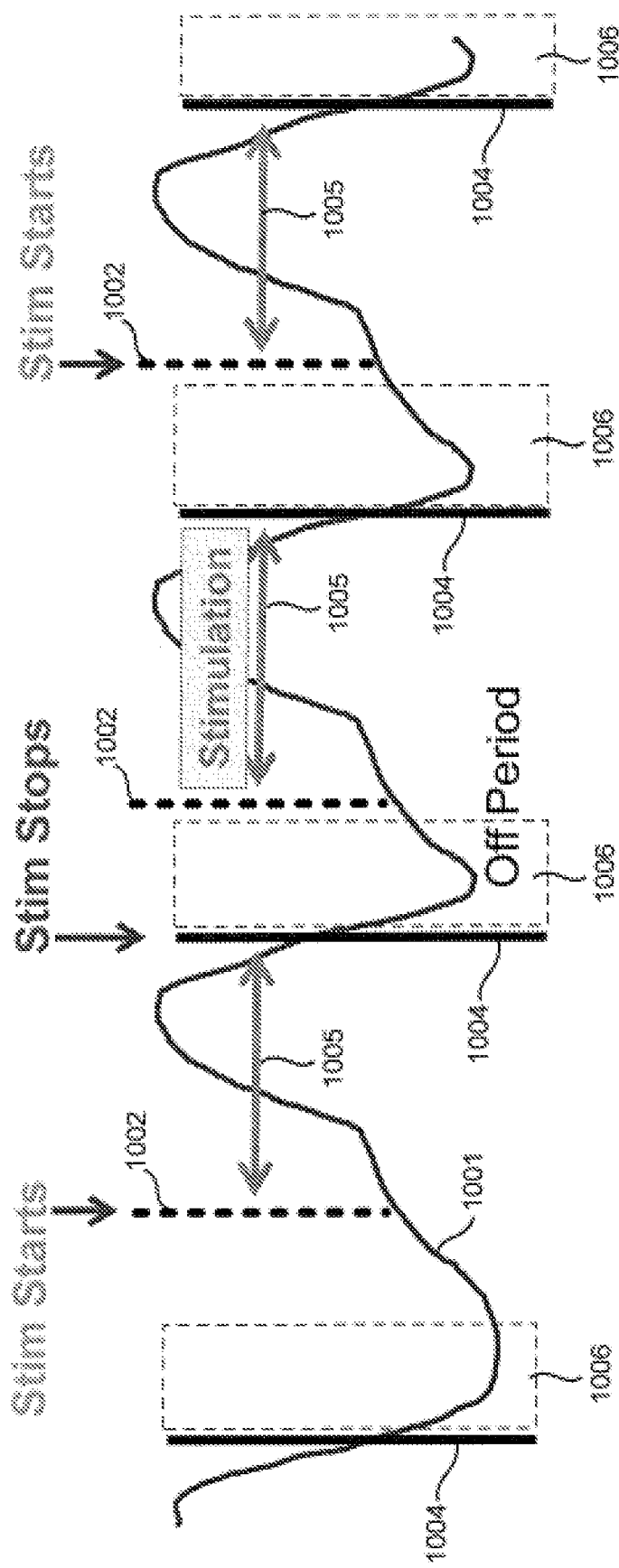
FIG. 10 shows an annotated respiratory waveform produced by a wireless programmer in accordance with various embodiments.

Embodiments of the present disclosure are directed to an annotated respiratory waveform produced by a wireless programmer of the type described hereinabove. An annotated respiratory waveform, such as that shown in FIG. 10, provides enhanced understanding of therapy delivered by an implantable neurostimulator to a patient suffering from obstructive sleep apnea (OSA). In particular, an annotated respiratory waveform provides an enhanced understanding of how an implantable neurostimulator is interpreting respiratory data during OSA therapy delivery. An annotated respiratory waveform of the present disclosure provides a visual indication of several important aspects of OSA therapy, including stimulation timing, inspiration detection, expiration detection, refractory (no detection) periods, and lack of inspiratory/expiratory detection, among other aspects. Annotation of respiratory waveforms using a wireless programmer provides the ability to record respiratory waveform data, to replay recorded respiratory waveform data, and to save and annotate respiratory waveform images. Annotation of respiratory waveforms using a wireless programmer also provides the ability to replay waveforms with different therapy parameters, and to visualize the impact of therapy changes.

FIG. 10 shows a respiratory waveform 1001 generated by an implantable neurostimulator in response to sensed intercostal muscle movement during patient breathing. FIG. 10 shows the respiratory waveform 1001 as it would be presented on a display of a wireless programmer of a type previously described. Superimposed over the respiratory waveform 1001 is annotation produced by the wireless programmer software. The annotation shown in FIG. 10 includes several different markers including a stimulation start marker 1002 (indicated by a dashed line) and a stimulation stop marker 1004 (indicated by a solid line). On the display of the wireless programmer, the stimulation start markers 1004 are colored blue and the stimulation stop markers 1004 are colored red according to some embodiments. The stimulation start and stop markers 1002 and 1004 allow the clinician to readily see the timing of stimulation start and stop events relative to recorded respiratory waveform features in real-time. The time between stimulation start and stop markers 1002 and 1004 represents the period of time during which stimulation is delivered to the patient. The annotated respiratory waveform shown in FIG. 10 further includes refractory periods 1006 (i.e., off periods) during which stimulation does not occur.

Figure 11:
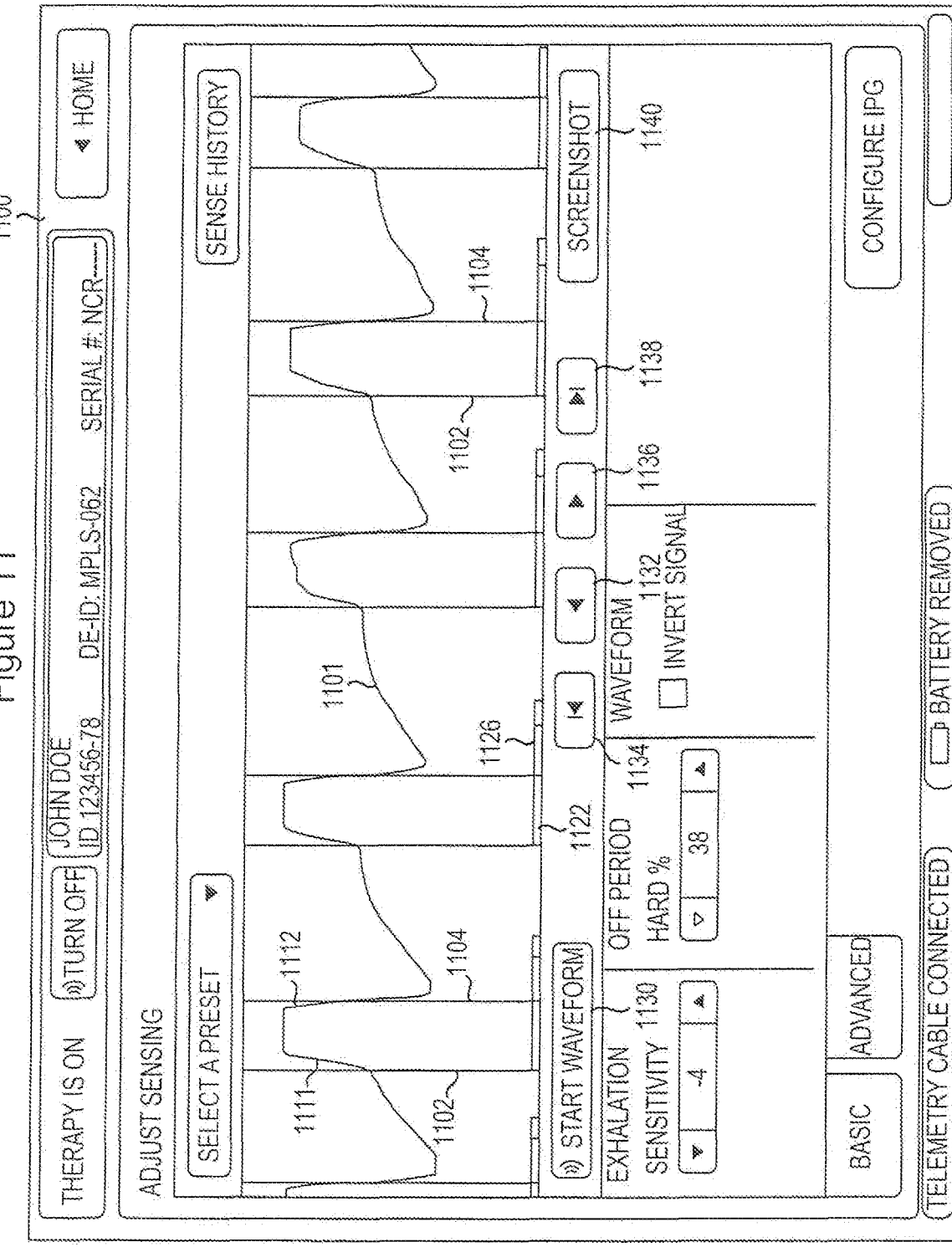
FIG. 11 shows an annotated respiratory waveform presented on a display of a wireless programmer in accordance with various embodiments.

FIG. 11 shows an annotated respiratory waveform 1101 presented on a display 1100 of a wireless programmer in accordance with various embodiments. The display 1100 includes a number of buttons that can be actuated by a user selection via a stylus or other implement. Activating the Start Waveform button 1130 causes viewing of a real-time respiratory waveform 1101 received from the implantable neurostimulator. As the respiratory waveform 1101 is presented on the display 1100, various markers and other information appear on the display 1100. Stimulation start markers 1002 (blue) and stimulation stop markers 1104 (*red*) are superimposed on the respiratory waveform 1101, respectively indicating the beginning and end of stimulation for each breath. Patient inhalation is indicated by upward going portions 1111 of the respiratory waveform 1101. Patient exhalation is indicated by downward going portions 1012 of the respiratory waveform 1101. Along the horizontal axis of the respiratory waveform chart region are additional markers, including a Stimulation On marker 1122 (green) and a Stimulation Off or refractory period marker 1126 (black/grey).

At a time, a screenshot of the current waveform can be stored by activation of the screenshot button 1140. The entire respiratory waveform recording can be navigated using various controls, including a back button 1132, a backwards button 1134, a forward button 1136, and a return-to-live-feed button 1138. Information about each waveform can be input and saved as part of the stored annotated respiratory waveform file. For a given respiratory waveform screenshot, such as that shown in FIG. 11, various contextual information can be recorded including, sleep type (e.g., Awake, Asleep, Anesthetized), patient position (e.g., Supine, Right, Left, Prone), polarity (Inspiration Up, Expiration Up, Other), and timing (e.g., Inspiratory Stimulation, Expiratory Stimulation, Other), for example. The clinician may store any number of respiratory waveforms as desired, including their associated annotation and contextual information (see, e.g., contextual information about stored respiratory waveform 1101 input via the screen shown in FIG. 12). The clinician may modify one or more parameters of the neurostimulator and immediately observe the impact of such parameter modifications on the annotated respiratory waveform. Modifying neurostimulator parameters and observing the results of such modifications in real time can occur during a simulation mode, rather than during actual therapy delivery.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. An apparatus for effecting communication with an implantable medical device, the apparatus comprising:
    a wireless programmer configured to interrogate and program the implantable medical device; and
    a telemetry apparatus, comprising:
        a communication channel comprising a plurality of disparate sequential communication links configured to facilitate bi-direction communication between the wireless programmer and the implantable medical device;
        a wireless transceiver configured to wirelessly communicate with the wireless programmer via a first communication link of the plurality of disparate communication links, the wireless transceiver including a transceiver housing;
        a telemetry device configured to wirelessly communicate with the implantable medical device via a second communication link of the plurality of disparate communication links, the telemetry device including a telemetry head housing, wherein the telemetry head housing is physically distinct from the transceiver housing;
        a third communication link communicatively coupling the wireless transceiver and the telemetry device, the third communication link including a wired cable extending between the transceiver housing and the telemetry head housing; and
        a power source coupled to the wireless transceiver and the telemetry device;
    wherein the wireless programmer is configured to individually determine an operational status of at least the first and second communication links in real-time.

2. The apparatus of claim 1, wherein the first communication link comprises a short-range radio frequency link capable of transmission through a structure of a building.

3. The apparatus of claim 1, wherein the telemetry apparatus is configured for operation only with a particular wireless programmer to which the telemetry apparatus is paired.

4. The apparatus of claim 1, wherein the wireless programmer is configured to prevent use of the second communication link in response to loss or non-establishment of the first communication link.

5. The apparatus of claim 1, wherein the wireless programmer is configured to transmit predetermined signals to individually determine the operational status of at least the first and second communication links.

6. The apparatus of claim 1, wherein the telemetry apparatus is configured to self-monitor its connectivity with the wireless programmer and the implantable medical device, and to indicate a status of said connectivity.

7. The apparatus of claim 1, wherein each of the wireless transceiver and the telemetry device is configured to self-monitor its connectivity with the wireless programmer and to indicate its connectivity status.

8. The apparatus of claim 1, wherein:
    the wireless transceiver comprises a connector configured to matingly engage a connector of the power source;
    the third communication link comprises a wired link between the wireless transceiver and the telemetry device; and
    power is supplied to the telemetry device from the wireless transceiver via the third communication link.

9. The apparatus of claim 1, wherein the telemetry device comprises a user control facility configured to facilitate manual control of one or more operations of the telemetry device.

10. The apparatus of claim 1, wherein the implantable medical device comprises an implantable neurostimulation device configured to treat obstructive sleep apnea.

11. The apparatus of claim 1, wherein:
the wireless transceiver further includes a transceiver status indicator carried by the transceiver housing to indicate an operational status of the wireless transceiver; and
the telemetry device further includes a telemetry device status indicator carried by the telemetry head housing to indicate an operational status of the telemetry device.

12. An apparatus for effecting communication between an implantable medical device and a programmer, the apparatus comprising:
a communication channel comprising a plurality of disparate sequential communication links configured to facilitate bi-direction communication between the implantable medical device and the programmer;
a transceiver configured to communicate with the programmer via a first communication link of the plurality of disparate communication links, the transceiver including a transceiver housing;
a telemetry device configured to communicate with the implantable medical device via a second communication link of the plurality of disparate communication links, the telemetry device including a telemetry head housing, wherein the telemetry head housing is physically distinct from the transceiver housing;
a third communication link communicatively coupling the transceiver and the telemetry device, the third communication link including a wired cable extending between the transceiver housing and the telemetry head housing; and
a power source coupled to the transceiver and to the telemetry device;
wherein an operational status of at least the first and second communication links can be individually determined in real-time.

13. The apparatus of claim 12, wherein the first communication link comprises a short-range radio frequency link capable of transmission through a building structure.

14. The apparatus of claim 12, wherein the first communication link conforms to one of a Bluetooth®, ZigBee® or Wi-Fi® communication protocol.

15. The apparatus of claim 12, wherein the second communication link conforms to one of an inductive, MICS or ISM communication protocol.

16. The apparatus of claim 12, wherein the apparatus is configured for operation only with a particular programmer to which the telemetry apparatus is paired.

17. The apparatus of claim 12, wherein the apparatus is configured to self-monitor its connectivity with the programmer and the implantable medical device, and to indicate a status of said connectivity.

18. The apparatus of claim 12, wherein each of the transceiver and the telemetry device is configured to self-monitor its connectivity with the programmer and to indicate its connectivity status.

19. The apparatus of claim 12, wherein:
the transceiver comprises a connector configured to matingly engage a connector of the power source;
the third communication link comprises a wired link between the transceiver and the telemetry device; and
power is supplied to the telemetry device from the transceiver via the third communication link.

20. The apparatus of claim 12, wherein:
the transceiver further includes a transceiver status indicator carried by the transceiver housing to indicate an operational status of the transceiver; and
the telemetry device further includes a telemetry device status indicator carried by the telemetry head housing to indicate an operational status of the telemetry device.

* * * * *